(12) United States Patent
Nakasugi

(10) Patent No.: US 7,648,809 B2
(45) Date of Patent: Jan. 19, 2010

(54) ELECTRON BEAM EXPOSURE METHOD, HOT SPOT DETECTING APPARATUS, SEMICONDUCTOR DEVICE MANUFACTURING METHOD, AND COMPUTER PROGRAM PRODUCT

(75) Inventor: Tetsuro Nakasugi, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 700 days.

(21) Appl. No.: 11/504,666

(22) Filed: Aug. 16, 2006

(65) Prior Publication Data

US 2007/0042513 A1 Feb. 22, 2007

(30) Foreign Application Priority Data

Aug. 17, 2005 (JP) ............................. 2005-236777

(51) Int. Cl.
*G03C 5/00* (2006.01)
*G03F 9/00* (2006.01)
(52) U.S. Cl. ..................... 430/30; 430/296; 430/942; 250/492.3
(58) Field of Classification Search .................. 430/30, 430/296, 942; 250/492.3
See application file for complete search history.

(56) References Cited

FOREIGN PATENT DOCUMENTS

| JP | 7-78737 | 3/1995 |
|----|---------|--------|
| JP | 10-275762 | 10/1998 |
| JP | 2004-31836 | 1/2004 |
| JP | 2005-159029 | 6/2005 |

*Primary Examiner*—Christopher G Young
(74) *Attorney, Agent, or Firm*—Finnegan, Henderson, Farabow, Garrett & Dunner, L.L.P.

(57) ABSTRACT

An EB exposure method includes dividing drawing layer pattern to be transferred onto drawing layer by EB exposure and underlying pattern to be transferred onto an underlying layer of the drawing layer by the EB exposure respectively into unit regions, setting representative figure in each of the unit regions of the drawing and underlying layers, the representative figure set in each of the unit regions of the drawing layer corresponding to the drawing layer pattern of each of the unit regions of the drawing layer, the representative figure set in each of the unit regions of the underlying layer corresponding to the underlying layer pattern of each of the unit regions of the underlying layer, and obtaining influence of proximity effect of an arbitrary region of the drawing layer pattern, based on the representative figure that corresponds to the drawing and underlying layer patterns.

16 Claims, 15 Drawing Sheets

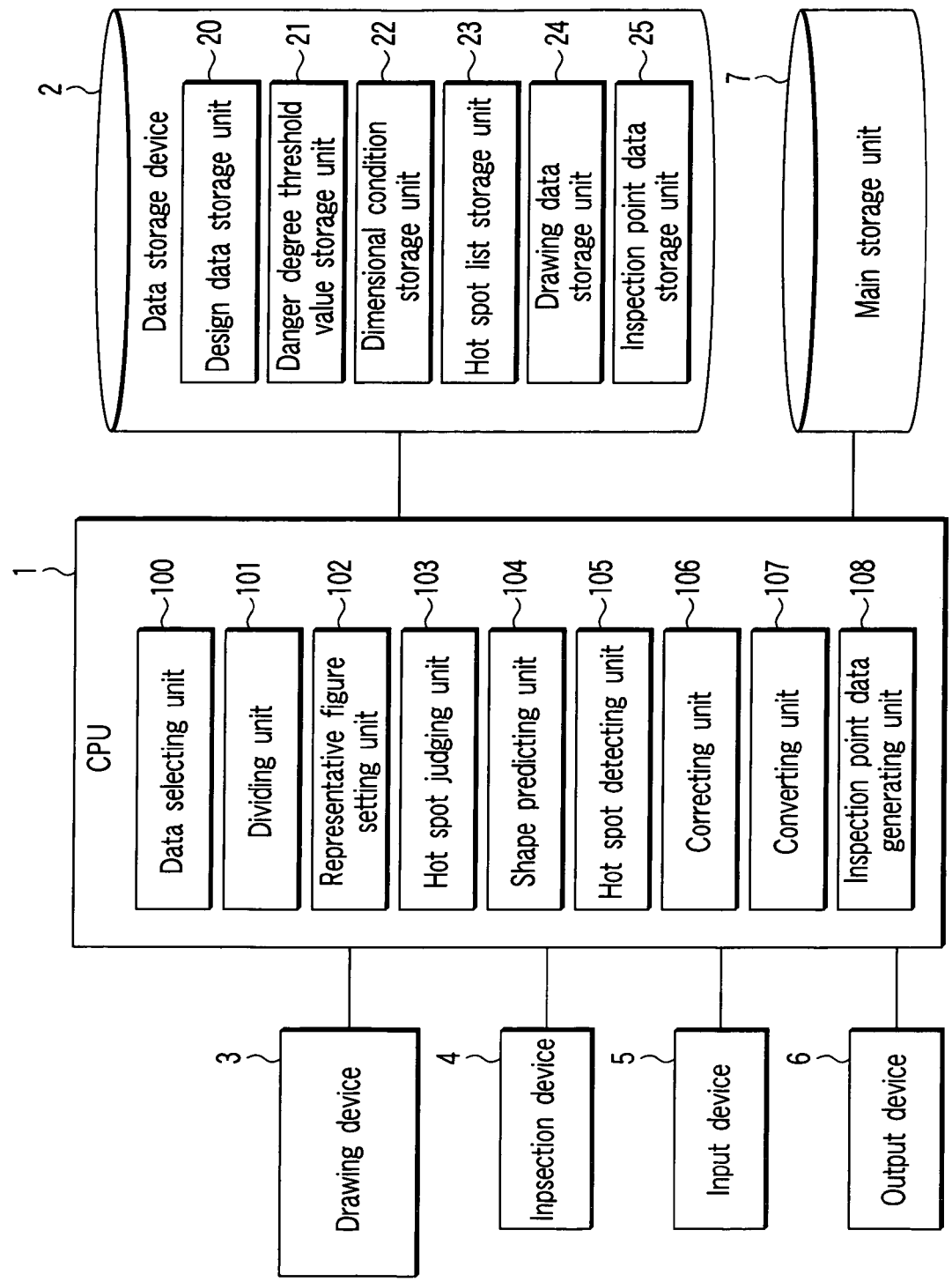
F I G. 1

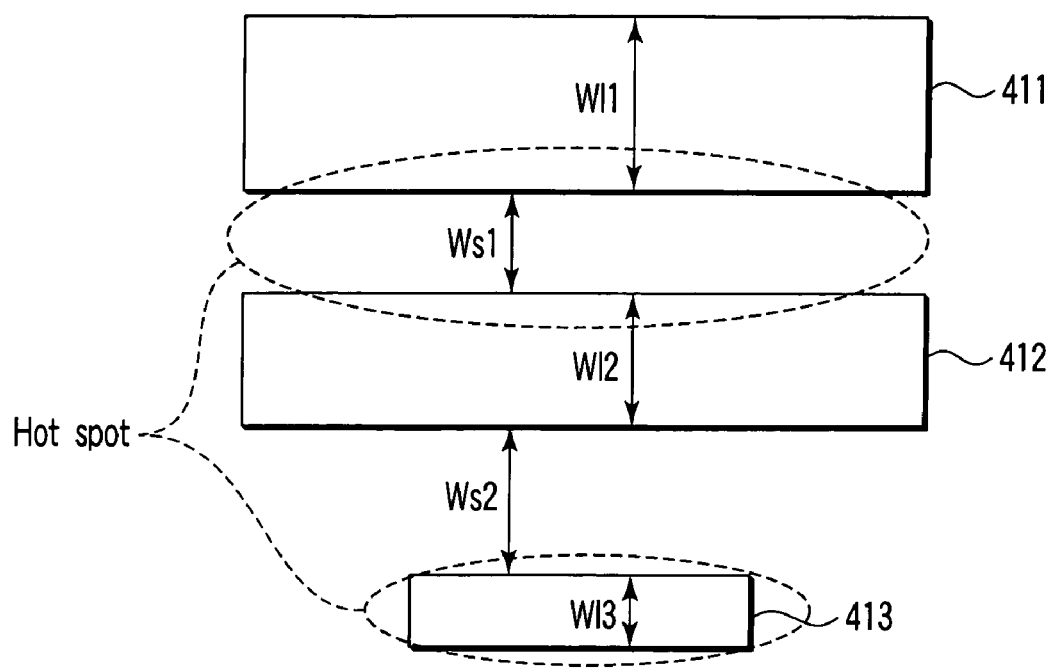
F I G. 13
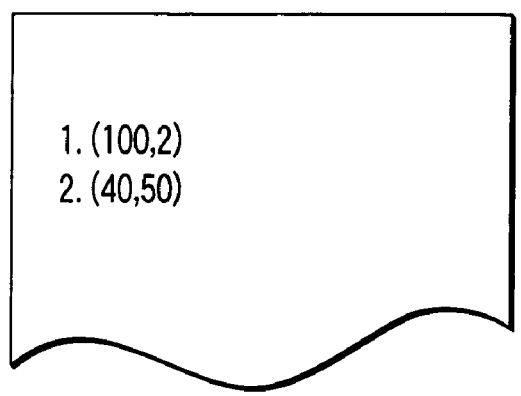
F I G. 14

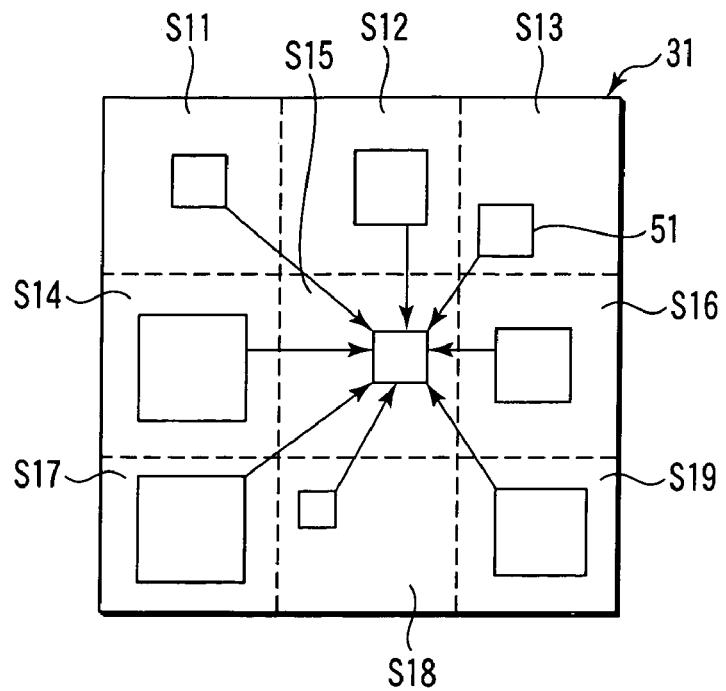
F I G. 17
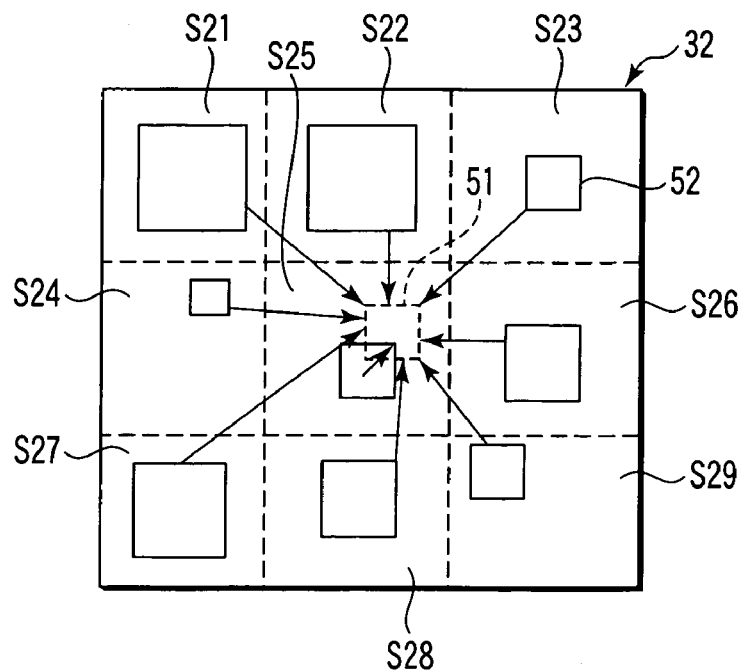
F I G. 18

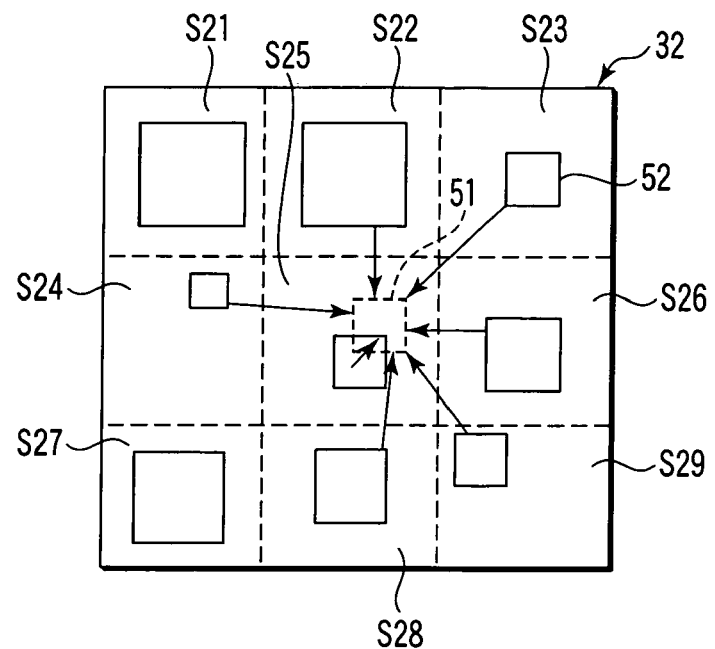
F I G. 21
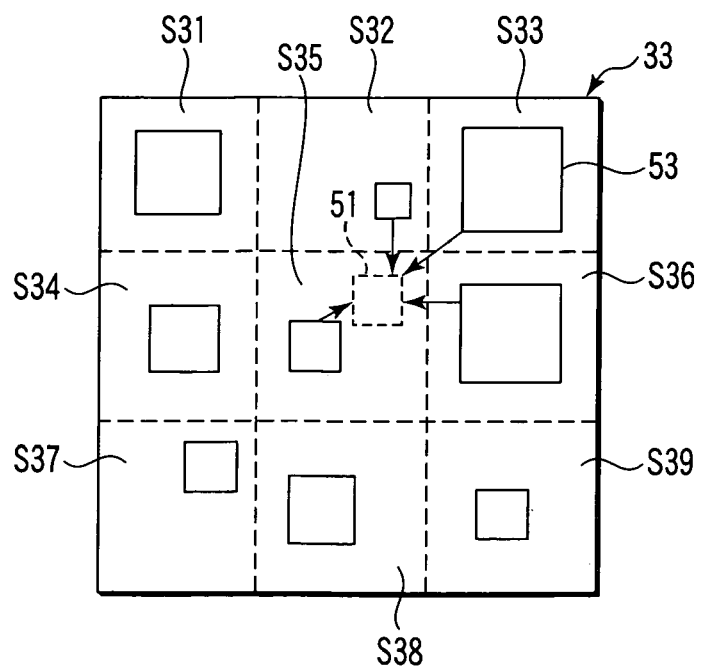
F I G. 22

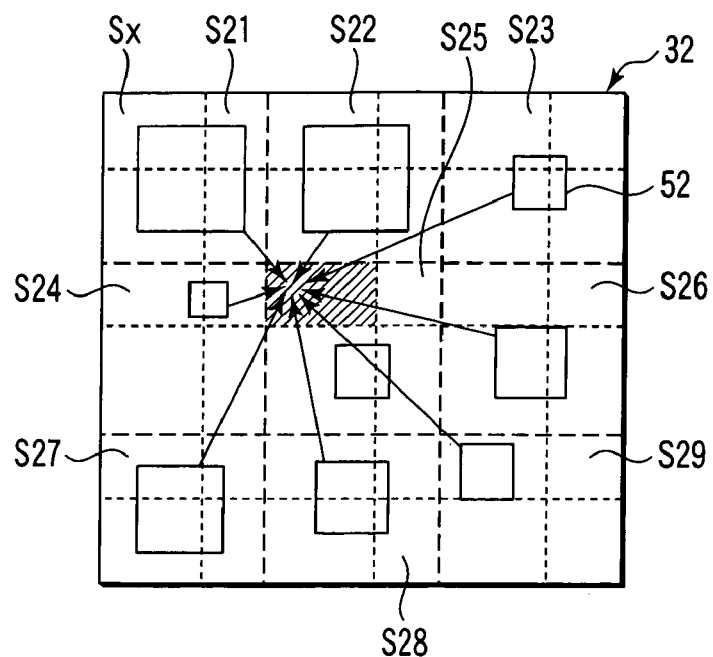
F I G. 25
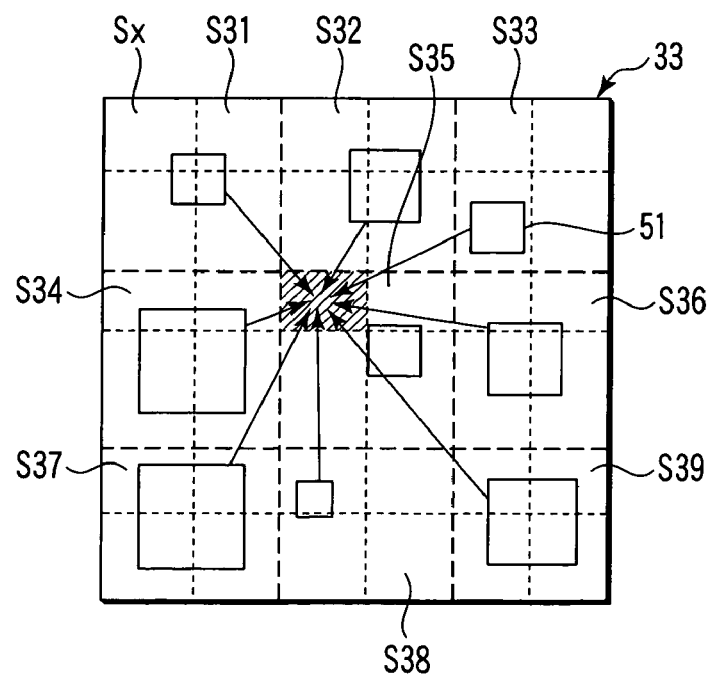
F I G. 26

ELECTRON BEAM EXPOSURE METHOD, HOT SPOT DETECTING APPARATUS, SEMICONDUCTOR DEVICE MANUFACTURING METHOD, AND COMPUTER PROGRAM PRODUCT

CROSS-REFERENCE TO RELATED APPLICATIONS

This application is based upon and claims the benefit of priority from prior Japanese Patent Application No. 2005-236777, filed Aug. 17, 2005, the entire contents of which are incorporated herein by reference.

BACKGROUND OF THE INVENTION

1. Field of the Invention

The present invention relates to an electron beam (EB) exposure technique, and particularly to an EB exposure method, a hot spot detecting apparatus, a semiconductor device manufacturing method, and a computer program product.

2. Description of the Related Art

In electron beam (EB) exposure, when EB is irradiated to a resist on a substrate, electrons expose the resist while scattering in the resist. Thereafter, the electrons collide with a substrate. The electrons having collided with the substrate are reflected due to elastic scattering. This reflection is referred to as "backward scattering", and the reflected electron is referred to as "backward scattering electron". Due to the backward scattering electrons, a region around an area of the resist irradiated with EB is also exposed. As a result, depending on the peripheral pattern area density, a fluctuation occurs with accumulated energy in the resist. The fluctuation of this accumulated energy may cause a fluctuation of dimensions of a resist pattern after developing and a fluctuation in finish dimensions of a pattern of a thin film layer (drawing layer) processed using the resist pattern as a mask. Thereafter, a phenomenon due to the backward scattering electrons is referred to as proximity effect. The correction for correcting an influence of proximity effect has been discussed.

It is necessary to carry out the proximity correction in consideration of a structure of an underlying layer that exists under a drawing layer as well as a structure of the drawing layer due to an effect of downsizing (Jpn. Pat. Appln. KOKAI Publication No. 2004-31836). However, the proximity correction considering the structure of the underlying layer requires a tremendously large amount of time and effort.

BRIEF SUMMARY OF THE INVENTION

According to an aspect of the present invention, there is provided an electron beam exposure method comprising: dividing a drawing layer pattern to be transferred onto a drawing layer by electron beam exposure and a underlying pattern to be transferred onto an underlying layer of the drawing layer by the electron beam exposure, respectively, into a plurality of unit regions; setting a representative figure in each of the plurality of unit regions of the drawing layer and the underlying layer, the representative figure set in each of the plurality of unit regions of the drawing layer corresponding to the drawing layer pattern of each of the plurality of unit regions of the drawing layer, the representative figure set in each of the plurality of unit regions of the underlying layer corresponding to the underlying layer pattern of each of the plurality of unit regions of the underlying layer; and obtaining influence of proximity effect of an arbitrary region of the drawing layer pattern, based on the representative figure corresponding to the drawing layer pattern and the underlying layer pattern.

According to an aspect of the present invention, there is provided a hot spot detecting apparatus comprising: a dividing unit configured to divide a drawing layer pattern to be transferred onto a drawing layer by electron beam exposure and a underlying pattern transferred to be onto an underlying layer of the drawing layer by the electron beam exposure, respectively, into a plurality of unit regions; a representative figure setting unit configured to set a representative figure in each of the plurality of unit regions of the drawing layer and the underlying layer, the representative figure set in each of the plurality of unit regions of the drawing layer corresponding to the drawing layer pattern of each of the plurality of unit regions of the drawing layer, the representative figure set in each of the plurality of unit regions of the underlying layer corresponding to the underlying layer pattern of each of the plurality of unit regions of the underlying layer; a hot spot judging unit configured to judge whether or not each of the plurality of unit regions of the drawing layer pattern is a hot spot, based on the representative figure corresponding to the drawing layer pattern and the underlying layer pattern; a shape predicting unit configured to predict a shape of a transferred pattern of the drawing layer pattern in the unit region judged to be the hot spot; and a hot spot detecting unit configured to detect a hot spot of the transferred pattern, based on the shape of the transfer pattern.

According to an aspect of the present invention, there is provided a semiconductor device manufacturing method comprising: forming an underlying layer on a substrate; forming a resist on the underlying layer; exposing the resist in accordance with an electron beam exposure method according to an aspect of the present invention; forming a resist pattern by developing the resist; and processing the underlying layer using the resist pattern as a mask.

According to an aspect of the present invention, there is provided a computer program product configured to store program instructions for execution on a computer system enabling the computer system to perform: an instruction for dividing a drawing layer pattern to be transferred onto a drawing layer by electron beam exposure and a underlying pattern to be transferred onto an underlying layer of the drawing layer by the electron beam exposure, respectively, into a plurality of unit regions; an instruction for setting a representative figure in each of the plurality of unit regions of the drawing layer and the underlying layer, the representative figure set in each of the plurality of unit regions of the drawing layer corresponding to the drawing layer pattern of each of the plurality of unit regions of the drawing layer, the representative figure set in each of the plurality of unit regions of the underlying layer corresponding to the underlying layer pattern of each of the plurality of unit regions of the underlying layer; an instruction for judging whether or not each of the plurality of unit regions of the drawing layer pattern is a hot spot, based on the representative figure that correspond to the drawing layer pattern and the underlying layer pattern; an instruction for predicting a shape of a transfer pattern of the drawing layer pattern in the unit region judged to be the hot spot; and an instruction for detecting a hot spot of the transfer pattern, based on the shape of the transfer pattern.

BRIEF DESCRIPTION OF THE SEVERAL VIEWS OF THE DRAWING

FIG. 1 is a block diagram depicting an example of a hot spot detecting apparatus according to an embodiment;

FIG. 13 is a schematic view showing an example of a predicted transfer pattern according to an embodiment;

FIG. 14 is a schematic view showing an example of a hot spot list according to an embodiment;

FIG. 17 is a schematic view of drawing layer data for explaining a method for setting a degree of danger according to a first modified example of an embodiment;

FIG. 18 is a schematic view of first underlying layer data for explaining a method for setting a degree of danger according to a first modified example of an embodiment;

FIG. 21 is a schematic view of first underlying layer data for explaining a method for setting a degree of danger according to a third modified example of an embodiment;

FIG. 22 is a schematic view of second underlying layer data for explaining a method for setting a degree of danger according to a third modified example of an embodiment;

FIG. 25 is a schematic view of first underlying layer data for explaining a method for setting a degree of danger according to a fourth modified example of an embodiment;

FIG. 26 is a schematic view for explaining an effect of proximity correction of second underlying layer data for explaining a method for setting a degree of danger according to a fourth modified example of an embodiment;

DETAILED DESCRIPTION OF THE INVENTION

Figure 2:
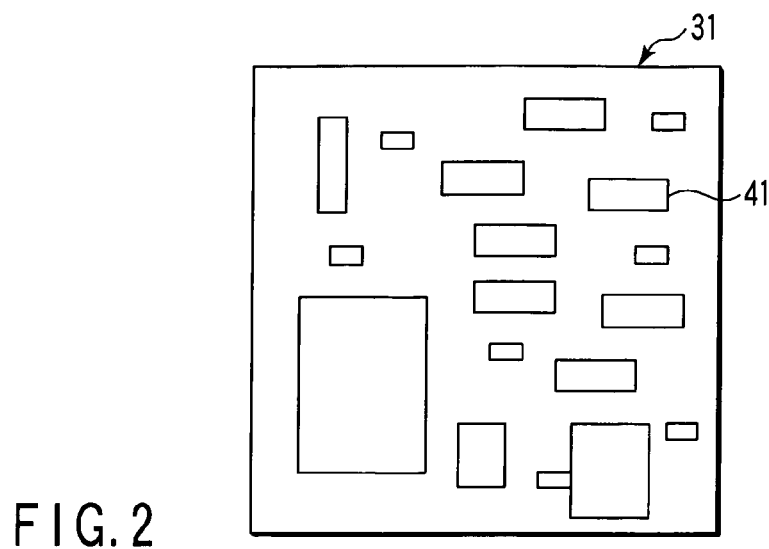
FIG. 2 is a schematic view depicting an example of drawing layer data according to an embodiment.

Now, an embodiment of the present invention will be described below with reference to the accompanying drawings. In the following description of the accompanying drawings, identical or like constituent elements are designated by identical or like reference numerals. It should be noted that the accompanying drawings are schematic and are different from reality in relationship between thickness and planar dimensions or in ratio of thickness of layers and the like.

A hot spot detecting apparatus according to the present embodiment, as shown in FIG. 1, comprises a central processing unit (CPU) 1; a data storage device 2; a drawing device 3; an inspection device 4; an input device 5; an output device 6; and a main storage device 7. The CPU 1 comprises a data selecting unit 100; a dividing unit 101; a representative figure setting unit 102; a hot spot judging unit 103; a shape predicting unit 104; a hot spot detecting unit 105; a correcting unit 105; a converter unit 107; and a inspection point (site) data producing unit 108.

Figure 3:
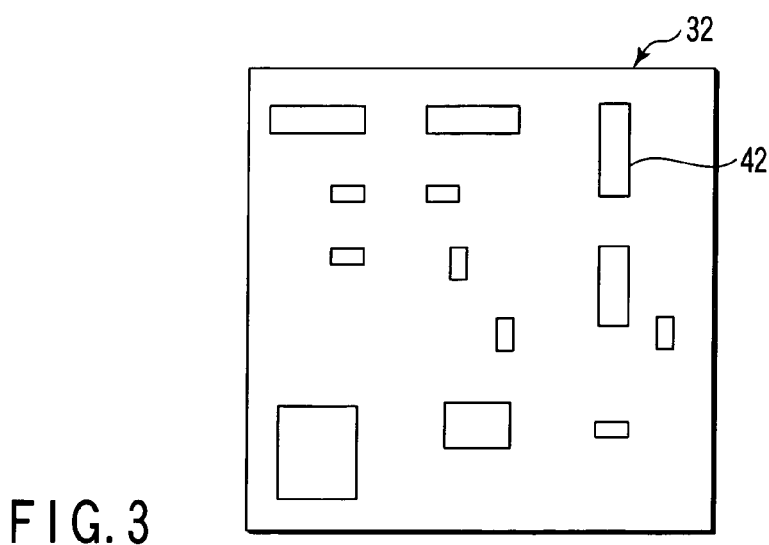
FIG. 3 is a schematic view depicting an example of first underlying layer data according to an embodiment.
Figure 4:
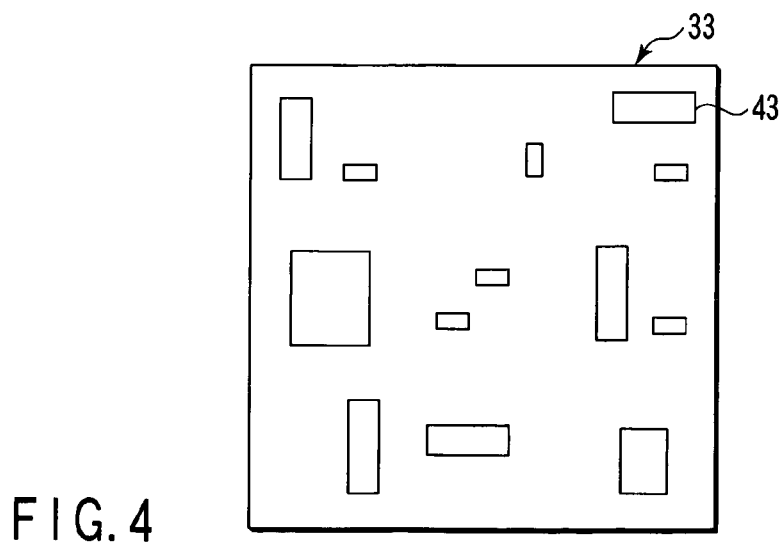
FIG. 4 is a schematic view depicting an example of second underlying layer data according to an embodiment.

The data selecting unit 100 selects drawing layer data 31 having drawn therein a plurality of drawing layer patterns 41 as shown in FIG. 2; first underlying layer data 32 having drawn therein a plurality of underlying layer patterns 42 as shown in FIG. 3; and second underlying layer data 33 having drawn therein a plurality of drawing layer patterns 43 as shown in FIG. 4, from among design data of layers stored in a design data storage unit 20 of the data storage device 2, based on an instruction inputted from the input device 5. FIGS. 2 and 3 schematically show the above patterns, and, in reality, it is a matter of course that a number of types/shapes of drawing layer patterns 41 and underlying layer patterns 42 and 43 are drawn.

Figure 5:
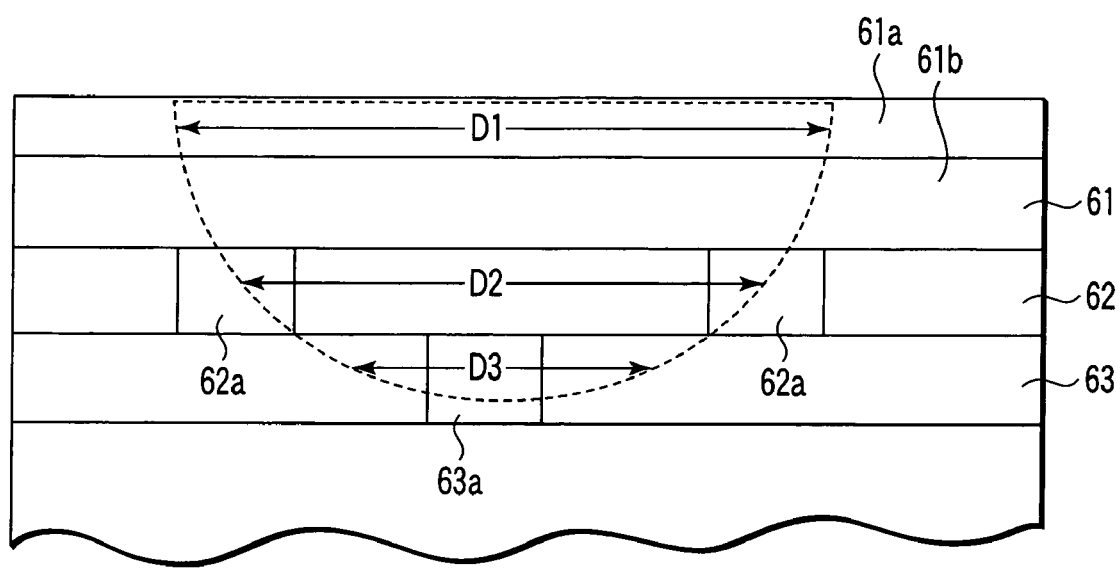
FIG. 5 is a schematic view of a drawing layer and an underlying layer for explaining backward scattering according to an embodiment.

The drawing layer pattern 41 of drawing layer data 31 and the underlying layer patterns 42 and 43 of first and second underlying layer data 32 and 33, as shown in FIG. 5, are transferred, respectively, to a thin film layer (drawing layer) 61 targeted for drawing, an underlying layer 62 formed beneath the drawing layer 61, and an underlying layer 63 formed under the underlying layer 62. In FIG. 5, 61a represents resist film, 61b represents a film to be processed, 62a and 63a represent underlying patterns. The backward electron scattering of EB spread from an irradiation point P in an isometric manner, and causes proximity effect. In order to correct proximity effect, it is important to predict a transfer pattern to be transferred onto the drawing layer 61 and detect a hot spot. Here, the drawing layer 61 is includes a silicon oxide film (or metal film such as Cu film, Al film, W film) on which a resist film 61a as a top layer is formed, the underlying layer 62 is a insulating film layer such as a silicon oxide film in which metal wiring formed of Cu, Al, W or like is embedded.

Figure 6:
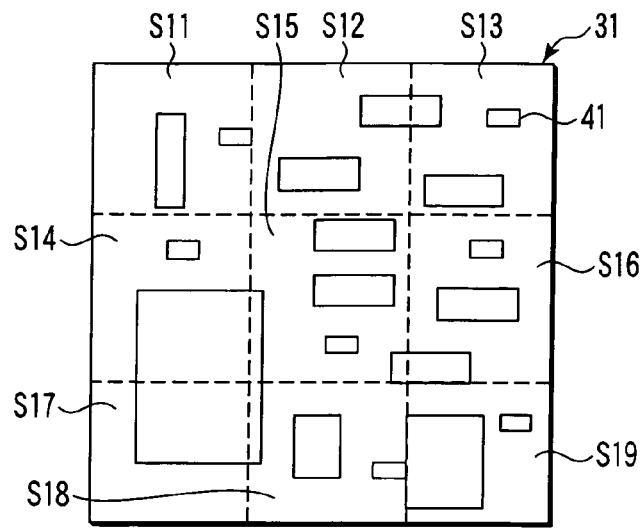
FIG. 6 is a schematic view showing an example of drawing layer data divided into unit regions according to an embodiment.

The dividing unit 101 shown in FIG. 1 divides drawing layer data 31 into unit regions S11 to S19, each of which has a size of 20 μm²×20 μm², as shown in FIG. 6. The unit regions S11 to S19 are set to be smaller than a maximum value of a backward scattering distance and to be greater than minimum pattern dimensions that can be drawn. Further, the dividing unit 101 divides first underlying layer data 32 into unit regions S21 to S29, as shown in FIG. 7; and divides second underlying layer data 33 into unit regions S31 to S39, as shown in FIG. 8.

Figure 9:
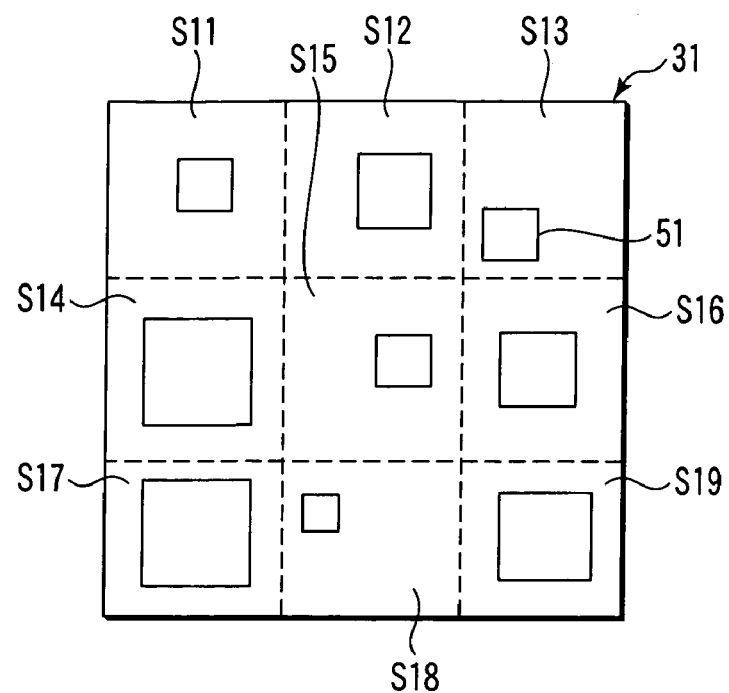
FIG. 9 is a schematic view showing an example of drawing layer data obtained when a representative figure according to an embodiment is set.

The representative figure setting unit 102 shown in FIG. 1 uses a representative figure technique, thereby setting one rectangle pattern obtained by adding all areas of the drawing layer pattern 41 in unit regions S11 to S19 as a representative figure 51, as shown in FIG. 9, respectively, by unit regions S11 to S19 of the drawing layer data 31 shown in FIG. 6. While positions in the unit regions S11 to S19 of the representative figure 51 are set at positions of center of gravity of all of the drawing layer patterns 41 in the unit regions S11 to S19 shown in FIG. 6, these positions each may be set at a central position of each of the unit regions S11 to S19.

Figure 7:
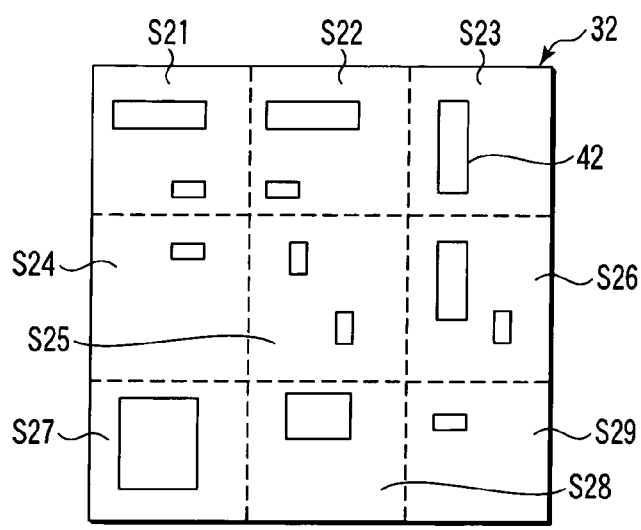
FIG. 7 is a schematic view showing an example of first underlying layer data divided into unit regions according to an embodiment.
Figure 8:
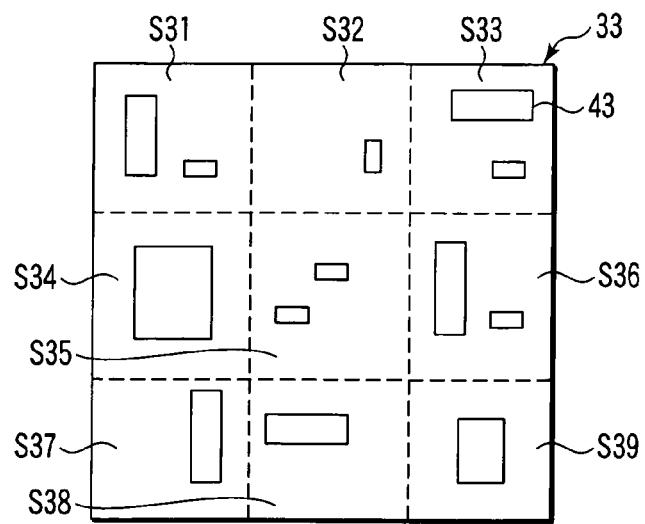
FIG. 8 is a schematic view showing an example of second underlying layer data divided into unit regions according to an embodiment.
Figure 10:
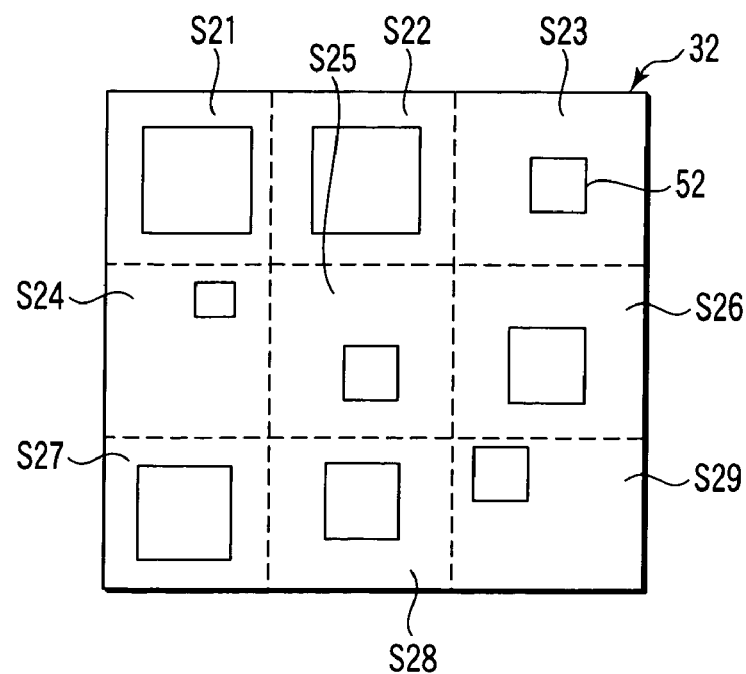
FIG. 10 is a schematic view showing an example of first underlying layer data obtained when a representative figure according to an embodiment is set.
Figure 11:
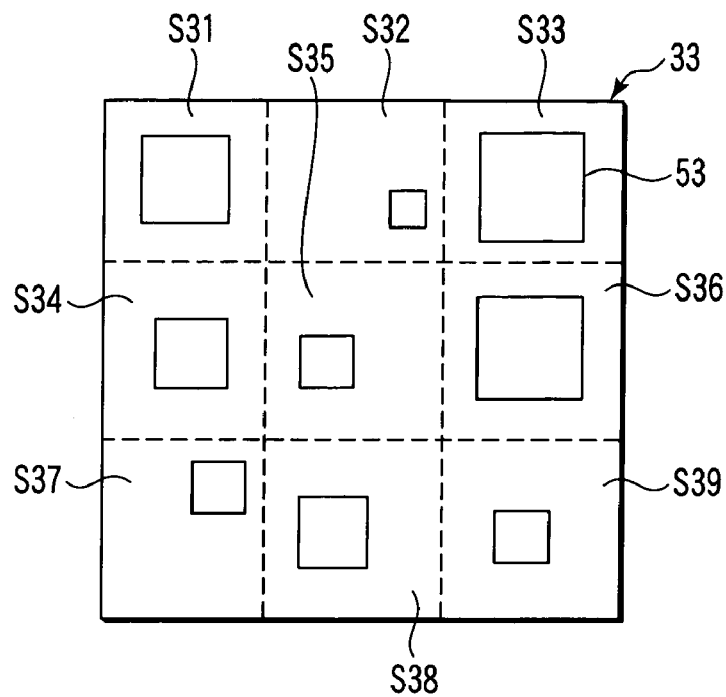
FIG. 11 is a schematic view showing an example of second underlying layer data obtained when a representative figure according to an embodiment is set.

Further, the representative figure setting unit 102 sets a representative figure 52 obtained by adding regions of the underlying layer patterns 42 in unit regions S21 to S29, as shown in FIG. 10 respectively, by unit regions S21 to S29 of the first underlying layer data 32 shown in FIG. 7. Further, the representative figure setting unit 102 sets a representative figure 53 obtained by adding areas of the underlying layer patterns 43 in unit regions S31 to S39, as shown in FIG. 11, respectively, by unit regions S31 to S39 of the second underlying layer data 33 shown in FIG. 8.

Figure 12:
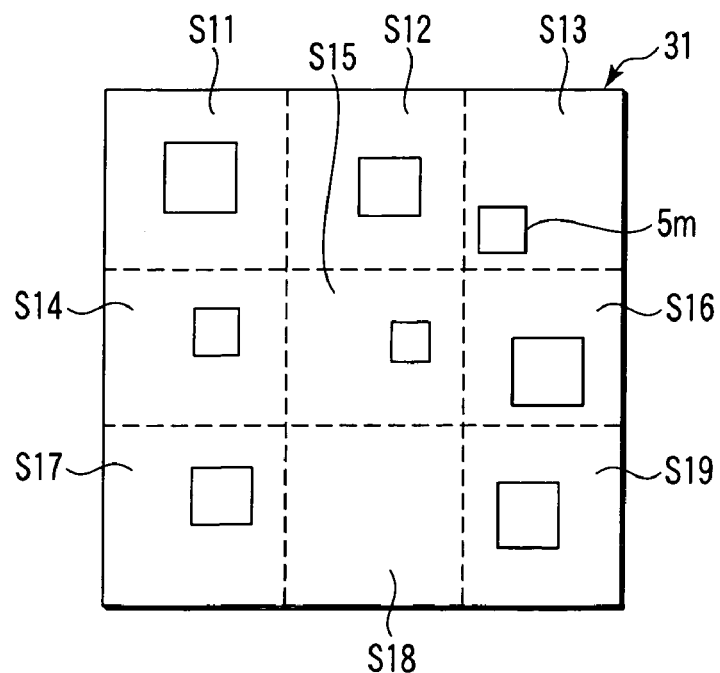
FIG. 12 is a schematic view showing an example of drawing layer data weighted and added according to an embodiment.

The hot spot judging unit 103 shown in FIG. 1 weights and adds an area of the representative figure 52 in unit regions S21 to S29 of the corresponding coordinate of the first underlying layer data 32 and an area of the representative figure 53 in unit regions S31 to S39 of the corresponding coordinate of the second underlying layer data 33, respectively, on an area of the representative figure 51 in unit regions S11 to S19 of the drawing layer data 31 by unit regions S11 to S19 of the drawing layer data 31:

$$\eta = \Sigma ai * Sij \quad (1)$$

where "ai" denotes a weight coefficient by layer; Sij (i=1 to 3, j=1 to 9) denotes areas of representative figure 51, 52, and 53 of unit regions S11 to S19, S21 to S29, and S31 to S39 of drawing layer data 31 and underlying layer data 32 and 33. For example, in the case where a heavy metal is used as underlying layer patterns 42 and 43, a value of the weight coefficient "ai" is increased. An proximity correction coefficient of each layer may be used for this weight coefficient "ai". The degree of influence of a proximal effect depends on a pattern area density. Thus, as shown in FIG. 12, an area η of a weighted representative FIG. 5m of the unit regions S11 to S19 of the drawing layer data 31 is calculated as a "degree of danger" showing an influence of the proximity effect in a stepwise manner.

Further, the hot spot judging unit 103 reads out a danger degree threshold value that serves as a criterion from a danger degree threshold value storage unit 22, and compares the danger degree threshold value and the danger degree η of the unit regions S11 to S19 with each other, respectively, thereby judging whether each of the unit regions S11 to S19 is a hot spot or not. The word "hot spot" denotes a unit region having a high possibility of including a dangerous region comprising pattern dimensions or a pattern interval at which desired specifications cannot be obtained. For example, in the case where the danger degree η of unit regions S11, S16, and S19 exceeds a danger degree threshold value, it is judged that the unit regions S11, S16, and S19 are hot spots. As a result, a "hot spot list" is generated, the list describing the unit regions S11, S16, and S19 judged to be hot spots.

The shape predicting unit 104 shown in FIG. 1 carries out a Monte Carlo simulation with respect to the unit regions S11, S16, and S19 described in the hot spot list, and then, calculates accumulated energy distributions of the drawing layer pattern 41 in unit regions S11 to S19 shown in FIG. 2, respectively. Further, the shape predicting unit 104 predicts transfer pattern shapes obtained when the drawing layer patterns 41 are transferred to drawing layers, respectively, by unit regions S11, S16, and S19, based on the accumulated energy distributions of the unit regions S11, S16, and S19. For example, the shape predicting unit 104 predicts line widths W11, W12, and W13 of transferred patterns 411, 412, and 413 or the shapes of inter-pattern dimensions Ws1 and Ws2 or the like as shown in FIG. 13, each of which corresponds to the drawing layer pattern 41 of the unit region S15. As a result, "shape prediction data" having described a shape of a predicted pattern is generated.

The hot spot detecting unit 105 shown in FIG. 1 reads out a dimensional condition such as a minimum line width or minimum gap dimensions from the dimensional condition storage unit 22. The hot spot detecting unit 105 compares a dimensional condition between dimensions W11, W12, and W13 of the transferred patterns 411, 412, and 413 described in shape predicting data and dimensions Ws1 and Ws2 between transferred patterns 411, 412, and 413, and then, detects a spot exceeding the dimensional condition as a hot spot. As a result, a "hot spot list" is generated, the list describing information relating to a hot spot such as a hot spot location in a unit region as shown in FIG. 14. The hot spot list can describe an intra-chip location of a unit region including a hot spot, the number of hot spots in a unit region, a mode such as a pattern dimension error or an intra-pattern dimension error, and a detail on each mode such as error dimensions from a set value or the like.

The correcting unit 106 shown in FIG. 1 design-changes and/or corrects patterns of the drawing layer data 31 or the underlying layer data 32 and 33 so as to eliminate a hot spot with respect to design data stored in the design data storage unit 20 and corrects and/or optimizes an irradiation dose when EB exposure is carried out. The converter unit 107 converts design data corrected so as to eliminate a hot spot into drawing data (electron beam drawing data). The converted drawing data is stored in a drawing data storage unit 24. The inspection point data producing unit 108 produces "inspection point data" having described a inspection point that corresponds to a hot spot to be inspected in a inspection step, based on a hot spot list stored in a hot spot list storage unit 23. The inspection point data is stored in an inspection point (site) data storage unit 25.

Further, the CPU 1 further comprises an input/output control device (interface), an exposure control unit, and a storage device management unit, although not shown. The input/output control device (interface) controls input/output of a signal or the like between the CPU 1, a drawing control unit, or the input device 5 and the output device 6. The exposure control unit reads out drawing data from the drawing data storage unit 24, and then, controls drawing by the drawing device 3 using EB. The storage device management unit manages input/output between the data storage device 2 and the main storage device 7.

The drawing device 3 irradiates EB with its optimized irradiation dose, and then, draws a resist pattern formed on a drawing layer, by using drawing data converted from design data by the converter unit 107.

The inspection device 4 inspects dimensions of a transfer pattern that corresponds to a drawing layer pattern judged to be a hot spot, from among the transferred patterns drawn by the drawing device 3, based on the inspection point data produced by the inspection point data producing unit 108.

As the input device 5, there can be used, for example, a recognition device such as a keyboard, a mouse, or an OCR; a graphics input device such as an image scanner; or a special input device such as a voice input device. The input device 5 inputs an instruction for drawing layer data targeted for drawing from a user, an instruction of the number of underlying layers to be considered under drawing layer data, and design data.

As the output device 6, there can be used a display device such as a liquid crystal display or a CRT display, or a printer device such as an ink jet printer or a laser printer. The output device 6 outputs a hot spot list relating to a hot spot detected by the hot spot detecting unit 105.

The data storage device 2 comprises a design data storage unit 20 that stores design data of each layer such as drawing layer data 32 and first and second underlying layer data 32 and 33, a danger degree threshold value storage unit 21 that stores a danger degree threshold value that serves as a criterion for a hot spot, a dimensional condition storage unit 22 that stores a dimensional condition such as a minimum line width or minimum gap dimensions of a transfer pattern, a hot spot list storage unit 23 that stores a hot spot list describing a hot spot detected by the hot spot detecting unit 105, a drawing data storage unit 24 that stores drawing data converted from design data by the converter unit 107, and a inspection point data storage unit 25 that stores inspection point data produced by the inspection point data producing unit 108.

The main storage device 7 temporarily stores data or the like utilized during program execution processing in the CPU 1 or functions as a temporary data memory or the like utilized as a work region. As the main storage device 7, there can be employed, for example, a semiconductor memory, a magnetic disk, an optical disk, a magneto-optical disk, a magnetic tape and the like.

Now, with reference to a flow chart of FIG. 15, a description will be given with respect to an EB exposure method including a hot spot detecting method according to an embodiment using a hot spot detecting apparatus shown in FIG. 1.

(A) In step S10, the data selecting unit 100 shown in FIG. 1 selects drawing layer data 31 and first and second underlying layer data 32 and 33 as shown in FIGS. 2, 3, and 4, respectively, from the design data storage unit 20 of the data storage device 2, based on instruction information from the input device 5. In step S11, the dividing unit 101 shown in FIG. 1 divides drawing layer data 31 and first and second underlying layer data 32 and 33 into unit regions S11 to S19, S21 to S29, and S31 to S39, respectively, as shown in FIGS. 6, 7, and 8.

(B) In step 12, a representative figure setting unit 102 shown in FIG. 1 sets representative figure 51 obtained by adding all areas of drawing layer patterns 41 in unit regions S11 to S19, respectively, by unit regions S11 to 19 of drawing layer data 31, as shown in FIG. 9. Further, the representative figure setting unit 102, as shown in FIG. 10, sets representative figure 52 obtained by adding areas of underlying layer patterns 42 in unit regions S21 to S29 by unit regions S21 to S29 of the first underlying layer data 32, respectively. Further, the representative figure setting unit 102, as shown in FIG. 11, sets representative figure 53 obtained by adding areas of underlying layer patterns 43 in unit regions S31 to S39 by unit regions S31 to S39 of the second underlying layer data 33, respectively.

(C) In step S13, the hot spot judging unit 103 shown in FIG. 1 uses formula (1) to weight and add an area of the representative figure 52 in unit regions S21 to S29 of the first underlying layer data 31 and an area of the representative figure 53 in unit regions S31 to S39 of the second underlying layer data 33 to an area of the representative figure 51 in unit regions S11 to S19 of the drawing layer data 31. As a result, an area $\eta$ of the representative FIG. 5$m$ shown in FIG. 12 is calculated as a degree of danger in each of the unit regions S11 to S19 of the drawing layer data 31. Further, the hot spot judging unit 103 reads out a danger degree threshold value from a dimensional condition storage unit 22, and then, compares a dimensional condition and danger degree $\eta$ of the unit regions S11 to S19 with each other. Then, the hot spot judging unit 103 judges the unit regions S11, S16, and S19, for example, whose danger degree $\eta$ exceeds the dimensional condition, as a hot spot, and generates a hot spot list.

(D) In step S14, the shape predicting unit 104 shown in FIG. 1 carries out a Monte Carlo simulation with respect to unit regions S11, S16, and S19 described in a hot spot list, and then, calculates accumulated energy distributions of the drawing layer pattern 41 in unit regions S11 to S19 shown in FIG. 2, respectively. Further, the shape predicting unit 104 predicts the shapes of transferred patterns 411, 412, and 413 obtained when the drawing layer pattern 41 is transferred to a resist, respectively, and then generates shape prediction data, as shown in FIG. 13, for example, by unit regions S1, S16, and S19, based on the accumulated energy distributions of the unit regions S11, S16, and S19.

(E) In step S15, the hot spot detecting unit 105 shown in FIG. 1 reads out a dimensional condition from a dimensional condition storage unit 22. The hot spot detecting unit 105 compares dimensions W11, W12, and W13 of transferred patterns 411, 412, and 413 described in shape prediction data with dimensions Ws1 and Ws2 between a minimum line width and minimum gap dimensions that are dimensional conditions. Then, in step S16, the hot spot detecting unit 105 detects a point (site) exceeding a dimensional condition as a hot spot, and then, generates a hot spot list.

(F) In step S17, the correcting unit 106 shown in FIG. 1 design-changes and/or corrects patterns of drawing layer data 31 and underlying layer data 32 and 33 so as to eliminate a hot spot with respect to the design data stored in the design data storage unit 20. At this time, the correcting unit 106 may correct and/or optimize an irradiation dose of EB exposure. If no hot spot occurs in step S16, processing goes to step S18.

(G) In step S18, the converter unit 107 shown in FIG. 1 converts the design data corrected by the correcting unit 106 into drawing data. The converted drawing data is stored in a drawing data storage unit 24. The drawing device 3 uses the drawing data converted from the design data by the converter unit 107 to irradiate EB to a resist with the optimized irradiation dose, and then, carries out drawing onto the resist. Thereafter, the resist is developed, and a resist pattern is formed. An underlying layer is processed using the resist pattern as a mask, and then, a transfer pattern is formed.

(H) In step S19, the inspection point data producing unit 108 shown in FIG. 1 produces inspection point data having described an inspection point that corresponds to a hot spot to be inspected in an inspection step, based on a hot spot list stored in a hot spot list storage unit 23. The inspection point data is stored in an inspection point data storage unit 25. The inspection device 4 inspects dimensions of a transfer pattern judged to be a hot spot at a time point of detecting a hot spot, from among transferred patterns, based on the inspection point data produced by the inspection point data producing unit 108.

In the present embodiment, the transferred pattern shapes that correspond to the drawing layer patterns 41 in the unit regions S11, S16, and S19 judged to be hot spots are predicted. Thus, according to the present embodiment, predicted points can be significantly reduced without degrading prediction precision, as compared with a case in which the shapes of the patterns in all of the unit regions S11 to S19 are predicted. In this manner, it becomes possible to judge a hot spot at a high speed, and it becomes possible to improve productivity in EB exposure.

Figure 29:
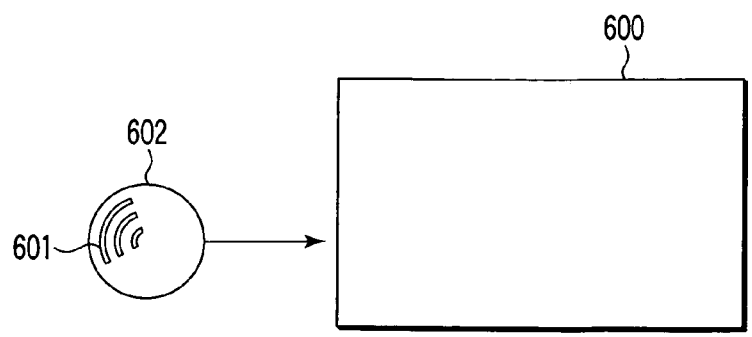
FIG. 29 is a view for explaining a computer program product according to an embodiment.

In addition, as shown in FIG. 29, the method according to the embodiment described above can be carried out as a computer program product 602 having recorded therein a program 601 to be executed by a system that includes a computer 600. The computer program product 602 includes: an instruction for dividing a drawing layer pattern transferred onto a drawing layer by electron beam exposure and an underlying pattern to be transferred onto an underlying layer of the drawing layer by the electron beam exposure, respectively, into a plurality of unit regions; an instruction for setting a representative figure in each of the plurality of unit regions of the drawing layer and the underlying layer, the representative figure set in each of the plurality of unit regions of the drawing layer being associated with the drawing layer pattern of each of the plurality of unit regions of the drawing layer, the representative figure set in each of the plurality of unit regions of the underlying layer being associated with the underlying layer pattern of each of the plurality of unit regions of the underlying layer; an instruction for judging whether or not each of the plurality of unit regions of the drawing layer pattern is a hot spot, based on the representative figure corresponding to the drawing layer pattern and the underlying layer pattern; an instruction for predicting a shape of a transferred pattern of the drawing layer pattern in the unit region judged to be the hot spot, and an instruction for detecting a hot spot of the transfer pattern, based on the shape of the transfer pattern.

Figure 15:
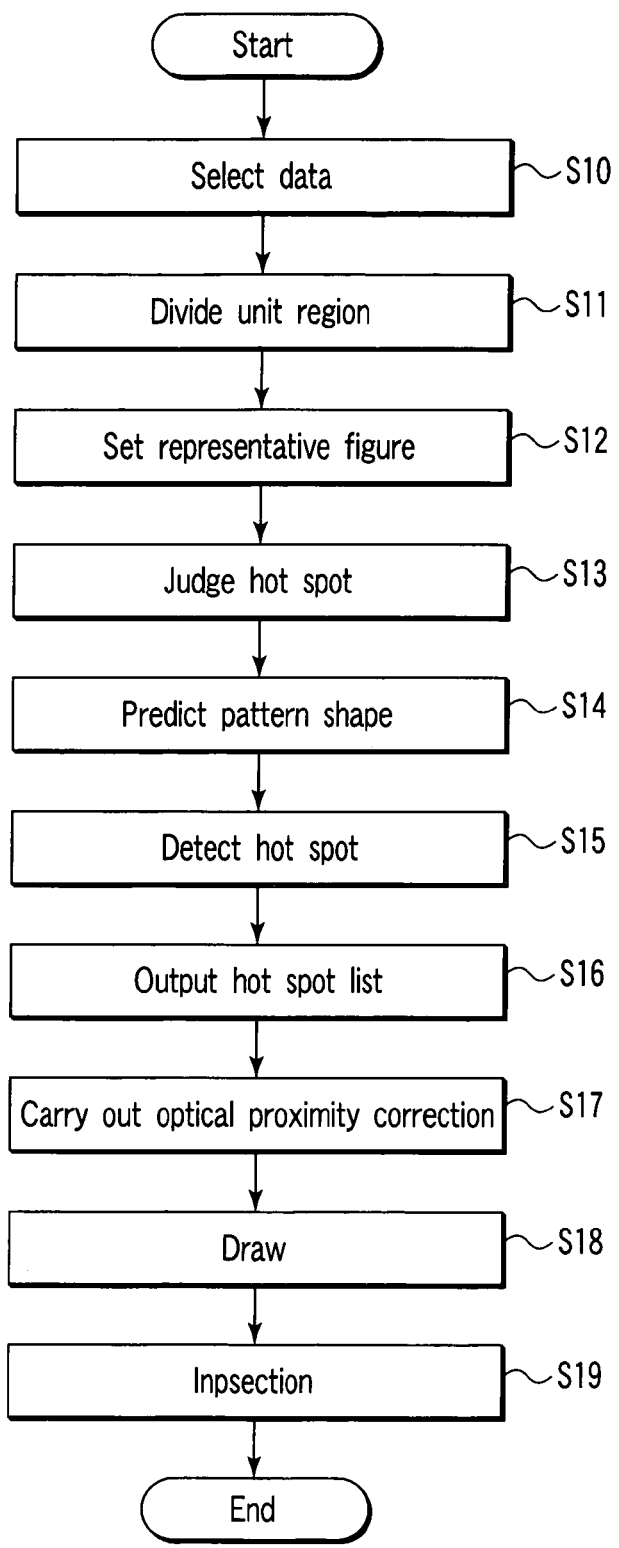
FIG. 15 is a flow chart for explaining an example of a depicting method including a hot spot detecting method according to an embodiment.

A series of procedures shown in FIG. 15 can be executed by controlling a hot spot detecting device shown in FIG. 1 in accordance with a program (hot spot detecting program) 601 that includes instructions shown in FIG. 15. In this case, the program 601 includes (A) an instruction for reading out a drawing layer pattern to be transferred onto a drawing layer by an electron beam drawing apparatus and an underlying layer pattern to be transferred onto an underlying layer of a drawing layer from a design data storage unit, and then dividing the drawing layer pattern and the underlying layer pattern, respectively, into a plurality of unit regions; (B) an instruction for setting a representative figure according to each of the drawing layer patterns and underlying layer patterns, respectively, for each unit region; (C) an instruction for judging whether or not a unit region of a drawing layer pattern is a hot spot, based on a representative figure; (D) an instruction for predicting a shape of a transferred pattern of a drawing layer pattern in a unit region judged to a hot spot; and (E) an instruction for detecting a hot spot of a transfer pattern, based on a shape of a transfer pattern. The program 601 may be stored in the data storage device 2 or the like. In addition, a series of procedures according to an embodiment can be executed by causing the data storage device 2 to read the computer program product 602 having the program 601 stored therein.

The term "computer program product" used here denotes a medium capable of recording a program such as a computer external memory device, a semiconductor memory, a magnetic disk, an optical disk, a magneto-optical disk, a magnetic tape, for example.

Specifically, a flexible disk, a CD-ROM, an MO disk and the like are included in the "computer program product".

For example, a main body of the data storage device 2 can be configured so as to incorporate or externally connect a flexible disk device (flexible disk drive) and an optical disk device (optical disk drive). A flexible disk is inserted into the flexible disk drive and a CD-ROM is inserted into an optical disk drive through its insert portion, and a predetermined readout operation is made, whereby programs stored in these storage mediums can be installed in the data storage device 2 that configures the drawing device 3. In addition, a ROM or a magnetic tape device can be used by connecting a predetermined drive device. Further, this program can be stored in the data storage device 2 via an information processing network such as the Internet.

Figure 16:
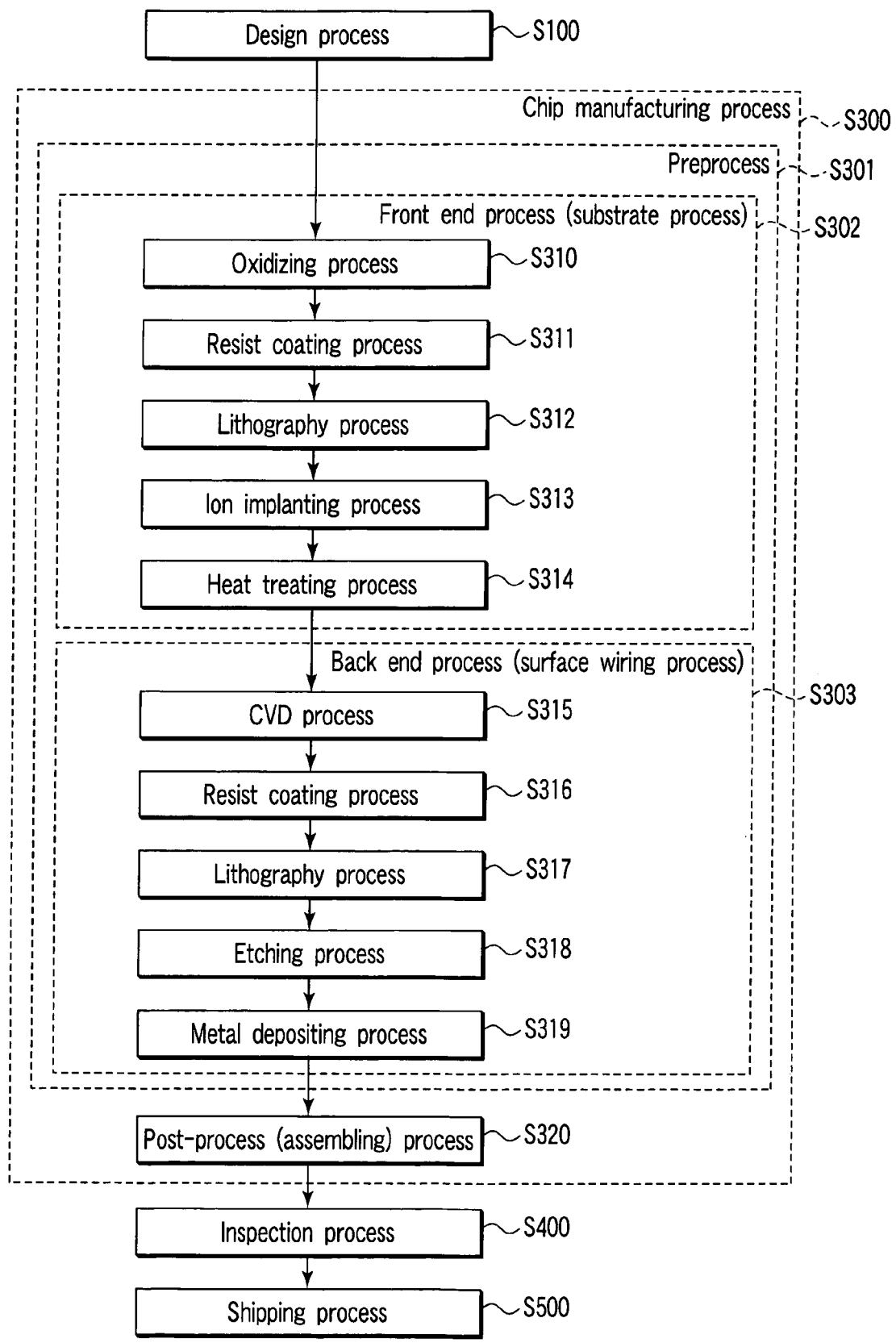
FIG. 16 is a flow chart for explaining a method for manufacturing a semiconductor device according to an embodiment.

Now, with reference to a flow chart of FIG. 16, a description will be given with respect to a method for manufacturing a semiconductor device according to the present embodiment using the hot spot detecting device shown in FIG. 1.

(A) First, in step S200, process mask simulation is carried out. Device simulation is made from a result of the process mask simulation and each value of a current or a voltage inputted to each electrode. LSI circuit simulation is carried out by using electrical characteristics obtained by device simulation, and design data of each layer is produced, the design data including drawing layer data 31 and first and second underlying layer data 32 and 33. Here, as in the procedures of the steps S10 to S17 shown in FIG. 15, a hot spot is detected by using the drawing layer data 31 and the first and second underlying layer data 32 and 33, and a hot spot list is outputted. Design data is corrected based on the hot spot list. The corrected design data is converted, respectively, producing drawing data for direct drawing for use in the drawing device 3 shown in FIG. 1.

(B) Next, in a front end process (substrate process) in step S302, an oxidizing process in step S310, a resist coating process in step S311, a lithography process by direct drawing method in step S312, an ion implanting process in step S313, and a heat treatment process or the like in step S314 are repeatedly carried out. When a series of processes finished, the processing goes to step S303.

(C) Next, in step S303, a back end process (surface wiring process) in which wiring processing is applied to a substrate surface is carried out. In the back end process, a chemical vapor deposition (CVD) process in step S315, a resist coating process in step S316, a lithography process by direct drawing method in step S317, an etching process in step S318, and a metal depositing process or the like in step S319 are repeatedly carried out. In steps S315 to S318, by using a CVD method, a lithography technique, an etching technique and the like, underlying layer patterns corresponding to the first and second underlying layer patterns 42 and 43 are formed on a semiconductor wafer. Further, in S315, a drawing layer targeted for transfer in the drawing layer 41 is deposited by CVD method or the like. In step S316, a photosensitive film (resist) is applied onto this drawing layer. In step S317, a semiconductor wafer is mounted on an exposure stage of the drawing device 3 shown in FIG. 1, and the drawing layer pattern 41 is drawn on a resist by the drawing device 3 using the drawing data corrected in step S200. Then, a resist is developed, and a resist pattern is formed. In step S318, a drawing layer is processed using a reactive ion etching (RIE) technique or the like using the resist pattern as a mask, and the drawing layer pattern 41 is transferred. Further, by the inspection device 4 shown in FIG. 1, a transferred pattern judged to be a hot spot may be inspected based on inspection point data. When a series of processes finished, processing goes to step S320.

(D) After a multi-layered wiring structure has been completed and a preprocessing process is finished, a wafer (substrate) is divided into a predetermined chip size by a dicing device such as a diamond blade in step S320. Then, after the divided wafer has been mounted on a package material such as a metal or a ceramics, and then, an electrode pad on a chip and a lead on a lead frame is connected to each other via a gold wire, a process for required package assembling such as resin sealing is carried out.

(E) In step S400, a semiconductor device is completed via characteristics inspection relating to performance/functions of a semiconductor device and predetermined inspection such as lead shape/dimensional state and reliability tests or the like. Here, by the inspection device 4 shown in FIG. 1, a transfer pattern judged to be a hot spot is inspected based on inspection point data. In step S500, a semiconductor device having cleared the above process is applied with a package for protection from moisture or static electricity and the like, and is shipped.

As described above, with a method for manufacturing a semiconductor device according to the present embodiment, the time and effort required for detecting a hot spot with respect to design data can be reduced in step S200. Therefore, throughput can be improved in the whole semiconductor manufacturing process.

The drawing device 3 shown in FIG. 1 may be utilized for fabricating an exposure mask. In this case, based on a surface pattern such as a layout designed in the design process of step S100, mask pattern data (drawing mask data) corresponding to each layer of a semiconductor chip and an internal structure are determined, respectively, by using a CAD system. With respect to this drawing mask data, a hot spot is detected in accordance with the procedures of steps S11 to S17 shown in FIG. 15, and proximity effect is corrected. By using the drawing device 3 (pattern generator) shown in FIG. 1, an exposure mask of each layer corresponding to each stage is fabricated on a mask substrate such as a quartz glass, and a mask set is prepared. In this case, in steps S312 and S317, for example, by using an exposure device (aligner), a pattern of an exposure mask of a corresponding layer is exposed onto a photosensitive film on a semiconductor wafer in accordance with a step and repeat method, and developed, and then, a resist pattern (etching mask) is fabricated.

According to the present embodiment, it becomes possible to judge a hot spot at a high speed in accordance with procedures or the like of step S100. Further, in the lithography process of step S317, a detected hot spot is corrected, and drawing is carried out by using drawing data. Thus, a failure is restricted. Further, in the inspection process of step S400, it becomes possible to precisely inspect hot spots. Therefore, the yields can be improved in the whole semiconductor manufacturing process, making it possible to improve productivity.

FIRST MODIFIED EXAMPLE

A first modified example of an embodiment describes another example of a method for setting a degree of danger of unit regions S11 to S19 of drawing layer data 31. The hot spot judging unit 103 shown in FIG. 1 selects a unit region S15, for example, from among the unit regions S11 to S19 of the drawing layer data 31 shown in FIG. 9. Further, the hot spot judging unit 103, as shown in FIG. 17, calculates influence (backward scattering electron dose) of proximity effect from a representative figure 51 in the peripheral unit regions S11 to S14 and S16 to S19 for a representative figure 51 in the unit region S15 of the drawing layer data 31.

Figure 19:
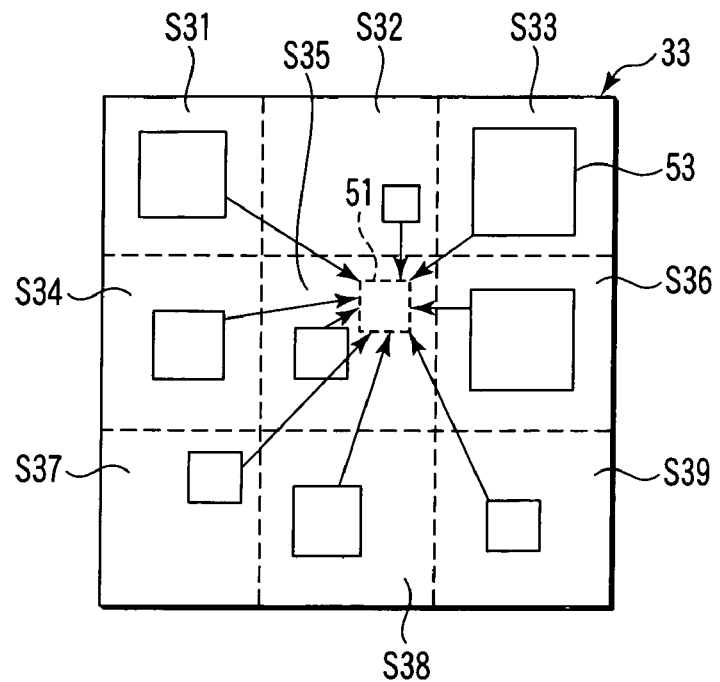
FIG. 19 is a schematic view of second underlying layer data for explaining a method for setting a degree of danger according to a first modified example of an embodiment.

Further, the hot spot judging unit 103, as shown in FIGS. 18 and 19, respectively, calculates influence the (backward scattering electron dose) of the proximity effect from representative figure 52 and 53 in each of the unit regions S21 to S29 and S31 to S39 of the first and second underlying layer data 32 and 33 with respect to the representative figure 51 in the unit region S15 of the drawing layer data 31. Further, the hot spot judging unit 103 calculates the influence (backward scattering electron dose) of the calculated proximity effect. The hot spot judging unit 103 adds the influence (back scattering electron dose) of the proximity effect from the representative figure 51 in the peripheral unit regions S11 to S14 and S16 to S19 with respect to the representative figure 51 in the unit region 51 of the calculated drawing layer data 31 and influence (backward scattering electron dose) of the proximal effect from the representative figure 52 and 53 in each of the unit regions S21 to S29 and S31 to S39 of the first and second underlying layer data 32 and 33, and sets the added influences as danger degrees of the unit region S15.

As in the unit region S15 of the drawing layer data 31, the degrees of danger are set with respect to the unit regions S11 to S14 and S16 to S19 as well. The rest of the configuration is substantially the same as the hot spot detecting device shown in FIG. 1, therefore a duplicate description is omitted here.

According to the first modified example of an embodiment, it becomes possible to set a degree of danger in consideration of the influence (backward scattering electron dose) of the proximity effect from the representative figure 51, 52, and 53 in the peripheral unit regions S11 to S19, S21 to S29, and S31 to S39 in layers for the unit regions S11 to S19.

SECOND MODIFIED EXAMPLE

A second modified example of an embodiment describes still another example of a method for setting degrees of danger of unit regions S11 to S19 of drawing layer data 31. The hot spot judging unit 103 shown in FIG. 1 weights and adds, as shown in FIG. 12, areas of representative figure 52 and 53 in each of the unit regions S21 to S29 and S31 to S39 that correspond to the underlying layer data 32 and 33 shown in FIGS. 10 and 11, respectively, to an area of a representative figure 51 of the unit regions S11 to S19 of drawing layer data 31 shown in FIG. 9, by using formula (1).

Figure 20:
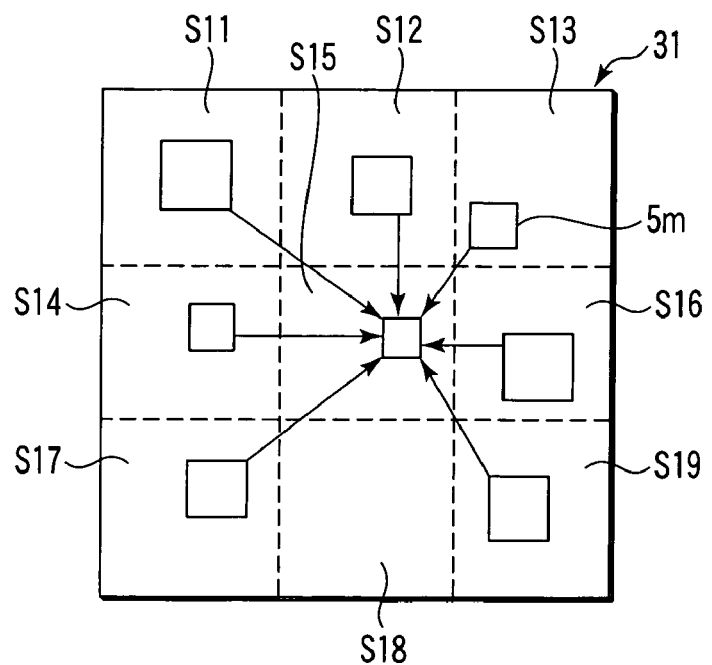
FIG. 20 is a schematic view of weighted drawing layer data for explaining a method for setting a degree of danger according to a second modified example of an embodiment.

Further, the hot spot judging unit 103 calculates the influence (backward scattering electron dose) of the proximity effect from a representative FIG. 5*m* of the peripheral unit regions S11 to S19 with respect to the unit regions S11 to S19 of the weighted and added drawing layer data 31 shown in FIG. 12. For example, the unit region S15 is selected. As shown in FIG. 20, the influence (backward scattering electron dose) of the proximity effect from the representative FIG. 5*m* in the peripheral unit regions S11 to S14 and S16 to S19 is calculated as a danger degree of the unit region S15. As in the unit region S15, the influence (backward scattering electron dose) of the proximity effect is calculated similarly with respect to the unit regions S11 to S14 and S16 to S19.

According to the second modified example of an embodiment, it becomes possible to calculate the influence (backward scattering electron dose) of the proximity effect from a representative FIG. 5m of the peripheral unit regions S11 to S19 in the weighted drawing layer data 31, and then, set a degree of danger.

THIRD EMBODIMENT

A third modified example of an embodiment describes still another example of a method for setting a degree of danger of unit regions S11 to S19 of drawing layer data 31. The number of patterns in a chip is increased due to downsizing, therefore several the tens of hours are required for only calculation of the influence of the proximity effect in a drawing layer 61. Thus, if a structure of underlying layers 62 and 63 is considered, the calculation time required for proximity correction increases in proportion to the number of considered underlying layers. Here, as shown in FIG. 5, backward scattering electrons spread in an isometric manner, and less reach the drawing layer 61 as they go to the underlying layers 62 and 63. Thus, when calculating influence of proximity effect, backward scattering distances D1, D2, and D3 can be set to be small as electrons go to the underlying layers 62 and 63 from the drawing layer 61.

The hot spot judging unit 103 shown in FIG. 1 sets the values of backward scattering electron distances D1, d2, and D3 to be small sequentially by the drawing layer data 31 and the first and second underlying layer data 32 and 33, based on an instruction and test data or the like inputted from an input device 5. For example, the backward scattering distances D1, D2, and D3 are set to 30 μm, 15 μm, and 5 μm, respectively.

Further, the hot spot judging unit 103 selects a unit region S15, for example, of the drawing layer data 31 shown in FIG. 9. The representative figure 51 of the unit regions S11 to S19 that exist in the range of the backward scattering distance D1 (=30 μm) is selected from the periphery of the selected unit region S15. Here, as shown in FIG. 17, all of the unit regions S11 to S19 are within the backward scattering distance D1 (=30 μm). The influence of the proximity effect from the selected unit regions S11 to S19 is calculated.

Further, the hot spot judging unit 103 selects a representative figure 52 of the unit regions S22, S23, S24, S25, S26, S28 and S29 that exist in the range of a preset backward scattering distance D2 (=15 μm) from the point of the first underlying layer data 32 shown in FIG. 10, which corresponds to the coordinate of the representative figure 51 of the unit region S15 of the drawing layer data 31. The influence of the proximal effect from the representative figure 52 of the selected unit regions S22, S23, S24, S25, S26, S28, and S29 is calculated as shown in FIG. 21.

Further, the hot spot judging unit 103 selects a representative figure 51 in the unit regions S32, S33, S35, and S36 that exist in the range of the preset backward scattering distance D3 (=5 μm) from the point of the second underlying layer data 33 shown in FIG. 11, which corresponds to the coordinate of the representative figure 51 of the unit region S15 of the drawing layer data 31. The influence of the proximity effect from the selected unit region S32, S33, S35, and S36 is calculated as shown in FIG. 22. Further, the hot spot judging unit 103 sets a degree of danger based on the influence of the calculated proximity effect.

According to the third modified example of an embodiment, the backward scattering distances D1, D2, and D3 are set by the drawing layer data 31 and the first and second underlying layer data 32 and 33, whereby the number of the peripheral representative figure considered at the time of calculating an inter-layered proximity effect can be reduced while considering the proximity effect from a relatively effective representative figure. Thus, it becomes possible to improve a calculation speed without degrading proximity correction precision.

FOURTH MODIFIED EXAMPLE

A fourth modified example of an embodiment describes still another example of a method for setting a degree of danger of unit regions S11 to S19 of drawing layer data 31.

Figure 23:
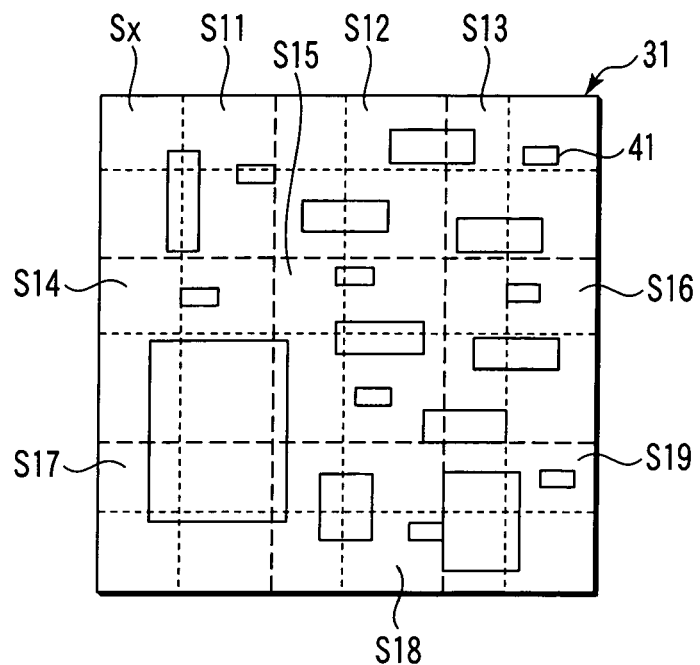
FIG. 23 is a schematic view of drawing layer data for explaining a method for setting a degree of danger according to a fourth modified example of an embodiment.

The dividing unit 101 shown in FIG. 1, as shown in FIG. 23, divides drawing layer data 31 into set regions Sx of size of 10×10 μm$^2$, for example, which is finer than the unit regions S11 to S19. Although the size of the set region Sx has been defined as 10×10 μm$^2$, for example, the size may be 1×1 μm$^2$ without being limited thereto. In addition, the size of the set region Sx may be adjusted so as to equally divide the unit regions S11 to S19 in consideration of the size of the unit regions S11 to S19.

Figure 24:
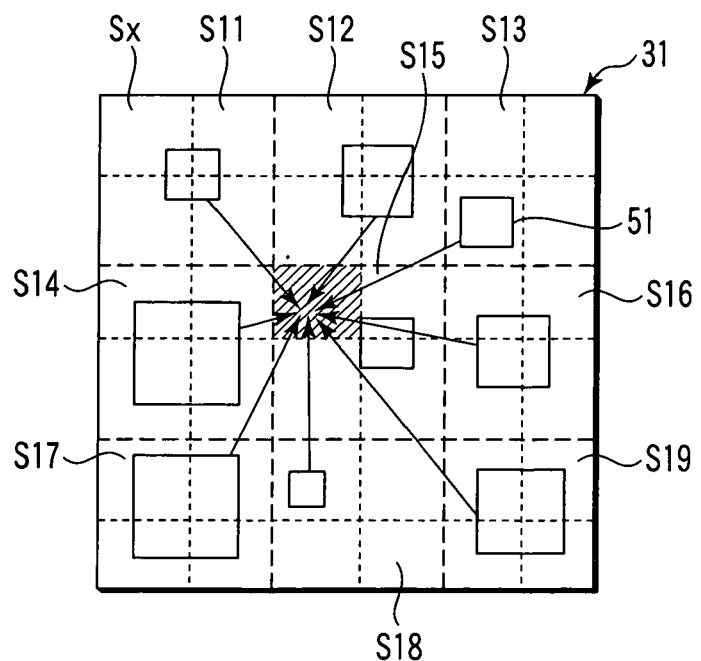
FIG. 24 is another schematic view of drawing layer data for explaining a method for setting a degree of danger according to a fourth modified example of an embodiment.

The hot spot judging unit 103 shown in FIG. 1 calculates the influence of the proximity effect from a representative figure 51 in the unit regions S11 to S19 with respect to the set region Sx on a set region Sx basis, as shown in FIG. 24. Further, the hot spot judging unit 103 calculates the influence of the proximity effect from a representative figure 52 in the unit regions S21 to S29 with respect to the set region Sx on a set region Sx basis, as shown in FIG. 25. Further, the hot spot judging unit 103 calculates the influence of the proximity effect from a representative figure 53 in the unit regions S31 to S39 with respect to the set region Sx on a set region Sx basis, as shown in FIG. 26.

Further, the hot spot judging unit 103 calculates the influences of the proximity effects from the representative figure 52 in the unit regions S21 to S29 and the representative figure 53 in the unit regions S31 to S39 with respect to the set region Sx on a set region Sx basis, as shown in FIG. 25. Further, the hot spot judging unit 103 sets the influence of the proximity effect calculated on a set region Sx basis and a degree of danger in each of the set regions Sx.

The shape predicting unit 104 shown in FIG. 1 predicts a pattern shape in units of set region Sx on a set region Sx basis judged to be a hot spot.

According to the fourth modified example of an embodiment, a hot spot can be detected more precisely by dividing it into the set region Sx that is finer than the unit regions S11 to S19, as compared with a case of dividing it into the unit regions S11 to S19.

Figure 27:
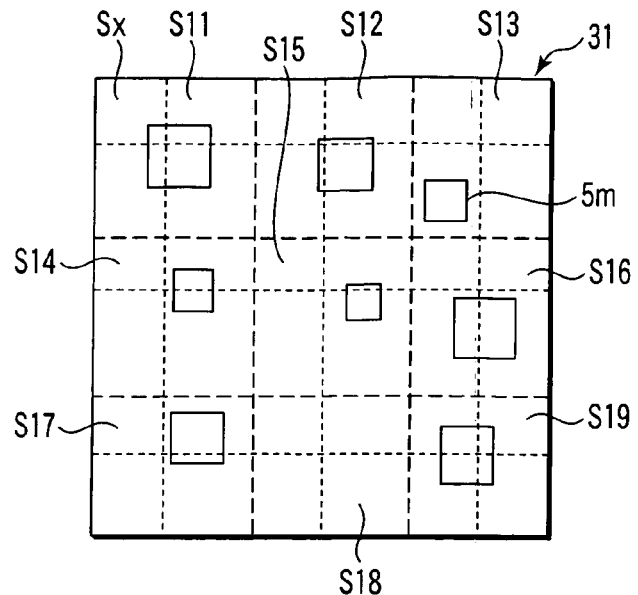
FIG. 27 is a schematic view showing an example of weighted drawing layer data for explaining a method for setting a degree of danger according to a fourth modified example of an embodiment.
Figure 28:
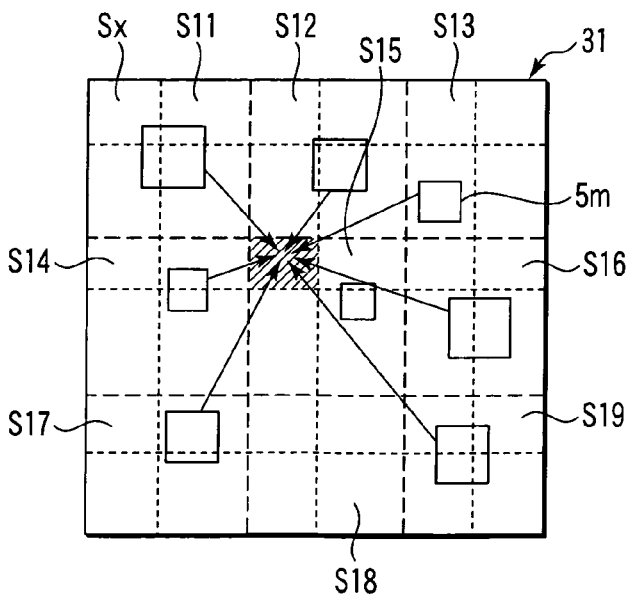
FIG. 28 is a schematic view depicting an example of drawing layer data divided into set regions for explaining a method for setting a degree of danger according to a fourth modified example of an embodiment.

The weighted drawing layer data 31 shown in FIG. 12 is divided into the set region Sx, as shown in FIG. 27, and then, the influence of the proximity effect is calculated as shown in FIG. 28, whereby a degree of danger may be set.

The present invention is not limited to the embodiments described above.

For example, the representative figure setting unit 102 shown in FIG. 1 adds a total area of the drawing layer pattern 41 and the underlying layer patterns 42 and 43 in each of the unit regions S11 to S19, S21 to S29, and S31 to S39, thereby having set the representative figure 51, 52, and 53. However, in addition to the total area, the representative figure 51, 52, and 53 according to at least any of the characteristics from among the total irradiation time obtained by multiplying the number of patterns, the number of shots, an accumulated irradiation time, an area of each shot, and an irradiation dose may be set by the unit regions S11 to S19, S21 to S29, and S31 to S39.

In addition, by the drawing layer pattern 41 shown in FIG. 2, the influence (back scattering electron dose) of the proximity effect from the representative figure 51, 52, and 53 in the unit regions S11 to S19, S21 to S29, and S31 to S39 shown in FIGS. 9, 10, and 11 fort the drawing layer pattern 41 is calculated, whereby a degree of danger may be set. By doing this, the influence of the proximity effect can be calculated along the drawing layer pattern 41.

In addition, the correcting unit 106 shown in FIG. 1 may carry out proximity correction calculation based on an output result of the hot spot judging unit 103 shown in FIG. 1.

For example, as described in the fourth modified example, the drawing layer data 31 is divided into the set region Sx of size of 1×1 μm², for example, which is finer than the unit regions S11 to S19. Further, in accordance with the method described in the second modified example, an area of a representative figure in each of the unit regions S21 to S29 and S31 to S39 of underlying layer data is weighted and added to each other as shown in FIG. 12, and the influence of the proximity effect for the set region Sx is calculated. Based on a result of the calculation, the correcting unit 106 can carry out proximity correction calculation.

In addition, the influence of the proximity effect for the set region Sx is calculated by using the method described in the third embodiment. Based on a result of the calculation, the correcting unit 106 may carry out proximity correction calculation.

Further, the size of the set region Sx shown in the fourth embodiment may be changed based on an output result of the hot spot judging unit 103 shown in FIG. 1. Specifically, the size of the set region Sx is reduced with respect to a region in which a degree of danger is great, and the size of the set region Sx is increased with respect to a region in which a degree of danger is small. By doing this, fine correction (irradiation dose or pattern dimensional correction) can be carried out with respect to a region in which a degree of danger is great, and drawing precision is improved.

In addition, the hot spot detecting unit 105 may generate a hot spot list based on the output result of the hot spot judging unit 103 shown in FIG. 1.

Further, the inspection point data producing unit 108 shown in FIG. 1 can also produce inspection point data having described an inspection point that corresponds to a hot spot, which should be inspected in an inspection process, based on a hot spot list generated based on the output result of the hot spot judging unit 103.

Although design data has been defined as input data, data in another format may be used. For example, exposure data of the drawing device 3 may be used. In addition, although processing has been carried out using a computer (CPU) shown in FIG. 1, another device may be used. The drawing device 3 may be used to produce a representative figure 51.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electron beam exposure method comprising:
   dividing a drawing layer pattern to be transferred onto a drawing layer by electron beam exposure and a underlying pattern to be transferred onto an underlying layer of the drawing layer by the electron beam exposure, respectively, into a plurality of unit regions;
   setting a representative figure in each of the plurality of unit regions of the drawing layer and the underlying layer, the representative figure set in each of the plurality of unit regions of the drawing layer corresponding to the drawing layer pattern of each of the plurality of unit regions of the drawing layer, the representative figure set in each of the plurality of unit regions of the underlying layer corresponding to the underlying layer pattern of each of the plurality of unit regions of the underlying layer; and
   obtaining influence of proximity effect of an arbitrary region of the drawing layer pattern, based on the representative figure corresponding to the drawing layer pattern and the underlying layer pattern.

2. The electron beam exposure method according to claim 1, wherein the obtaining the influence of the proximity effect includes calculating an attribute relating to the representative figure according to the drawing layer pattern, weighted by an attribute relating to the representative figure according to the underlying layer pattern.

3. The electron beam exposure method according to claim 2, wherein the attribute is an area.

4. The electron beam exposure method according to claim 1, wherein the obtaining the influence of the proximity effect includes setting a backward scattering distance according to the underlying layer pattern.

5. The electron beam exposure method according to claim 2, wherein obtaining influence of the proximity effect includes setting a backward scattering distance according to the underlying layer pattern.

6. The electron beam exposure method according to claim 3, wherein obtaining influence of the proximity effect includes setting a backward scattering distance according to the underlying layer pattern.

7. The electron beam exposure method according to claim 3, further comprising correcting design data that corresponds to the drawing pattern, based on the proximity effect.

8. A hot spot detecting apparatus comprising:
   a dividing unit configured to divide a drawing layer pattern to be transferred onto a drawing layer by electron beam exposure and a underlying pattern transferred to be onto an underlying layer of the drawing layer by the electron beam exposure, respectively, into a plurality of unit regions;
   a representative figure setting unit configured to set a representative figure in each of the plurality of unit regions of the drawing layer and the underlying layer, the representative figure set in each of the plurality of unit regions of the drawing layer corresponding to the drawing layer pattern of each of the plurality of unit regions of the drawing layer, the representative figure set in each of the plurality of unit regions of the underlying layer corresponding to the underlying layer pattern of each of the plurality of unit regions of the underlying layer;
   a hot spot judging unit configured to judge whether or not each of the plurality of unit regions of the drawing layer pattern is a hot spot, based on the representative figure corresponding to the drawing layer pattern and the underlying layer pattern;
   a shape predicting unit configured to predict a shape of a transferred pattern of the drawing layer pattern in the unit region judged to be the hot spot; and
   a hot spot detecting unit configured to detect a hot spot of the transferred pattern, based on the shape of the transfer pattern.

9. A semiconductor device manufacturing method comprising:
   forming an underlying layer on a substrate;
   forming a resist on the underlying layer;

exposing the resist in accordance with an electron beam exposure method of claim 1;

forming a resist pattern by developing the resist; and processing the underlying layer using the resist pattern as a mask.

10. The semiconductor device manufacturing method according to claim 9, wherein the obtaining the influence of the proximity effect includes calculating an attribute relating to the representative figure according to the drawing layer pattern, weighted by an attribute relating to the representative figure according to the underlying layer pattern.

11. The semiconductor device manufacturing method according to claim 10, wherein the attribute is an area.

12. The semiconductor device manufacturing method according to claim 9, wherein the obtaining the influence of the proximity effect includes setting a backward scattering distance according to the underlying layer pattern.

13. The semiconductor device manufacturing method according to claim 10, wherein obtaining influence of the proximity effect includes setting a backward scattering distance according to the underlying layer pattern.

14. The semiconductor device manufacturing method according to claim 11, wherein obtaining influence of the proximity effect includes setting a backward scattering distance according to the underlying layer pattern.

15. The semiconductor device manufacturing method according to claim 11, further comprising correcting design data that corresponds to the drawing pattern, based on the proximity effect.

16. A computer program product configured to store program instructions for execution on a computer system enabling the computer system to perform:

an instruction for dividing a drawing layer pattern to be transferred onto a drawing layer by electron beam exposure and a underlying pattern to be transferred onto an underlying layer of the drawing layer by the electron beam exposure, respectively, into a plurality of unit regions;

an instruction for setting a representative figure in each of the plurality of unit regions of the drawing layer and the underlying layer, the representative figure set in each of the plurality of unit regions of the drawing layer corresponding to the drawing layer pattern of each of the plurality of unit regions of the drawing layer, the representative figure set in each of the plurality of unit regions of the underlying layer corresponding to the underlying layer pattern of each of the plurality of unit regions of the underlying layer;

an instruction for judging whether or not each of the plurality of unit regions of the drawing layer pattern is a hot spot, based on the representative figure that correspond to the drawing layer pattern and the underlying layer pattern;

an instruction for predicting a shape of a transfer pattern of the drawing layer pattern in the unit region judged to be the hot spot; and an instruction for detecting a hot spot of the transfer pattern, based on the shape of the transfer pattern.

\* \* \* \* \*